United States Patent
Pinsky (10) Patent No.: US 6,776,764 B2
(45) Date of Patent: Aug. 17, 2004

(54) USE OF AORTIC PULSE PRESSURE AND FLOW IN BEDSIDE HEMODYNAMIC MANAGEMENT

(75) Inventor: Michael R. Pinsky, Pittsburgh, PA (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 10/098,655

(22) Filed: Mar. 15, 2002

(65) Prior Publication Data

US 2003/0167010 A1 Sep. 4, 2003

Related U.S. Application Data

(63) Continuation-in-part of application No. 10/086,343, filed on Mar. 1, 2002, now abandoned.

(51) Int. Cl.[7] .................................................. A61B 5/02
(52) U.S. Cl. ........................ 600/481; 600/301; 600/485
(58) Field of Search ................................. 600/300, 301, 600/481, 485–507, 508; 604/65–67

(56) References Cited

U.S. PATENT DOCUMENTS

| | | | | |
|---|---|---|---|---|
| 5,370,122 A | * | 12/1994 | Kunig et al. ................. 600/483 |
| 5,810,011 A | * | 9/1998 | Kunig .......................... 600/481 |
| 5,900,433 A | * | 5/1999 | Igo et al. ...................... 514/530 |
| 6,112,115 A | * | 8/2000 | Feldman et al. ............. 600/513 |
| 6,217,522 B1 | * | 4/2001 | Shoshan ....................... 600/490 |
| 6,270,461 B1 | * | 8/2001 | Chio ............................ 600/485 |
| 6,287,608 B1 | * | 9/2001 | Levin et al. ................. 424/718 |
| 6,315,735 B1 | * | 11/2001 | Joeken et al. ............... 600/500 |
| 6,334,849 B1 | * | 1/2002 | Sunagawa .................... 600/485 |
| 6,339,716 B1 | * | 1/2002 | Sawada et al. .............. 600/407 |
| 6,371,922 B1 | * | 4/2002 | Baumann et al. ............ 600/485 |
| 6,485,431 B1 | * | 11/2002 | Campbell .................... 600/526 |

* cited by examiner

Primary Examiner—Patricia Mallari
(74) Attorney, Agent, or Firm—Amster, Rothstein & Ebenstein LLP (57) ABSTRACT

A treatment algorithm for managing hemodynamically unstable patients is provided. Specifically, measurements of arterial pressure and stroke volume can be used to calculate pulse pressure variation, stroke volume variation, mean arterial pressure, elastance and cardiac power, the values of which guide treatment decisions and allow optimal management of critically ill patients. In an additional embodiment, a computer system implementing the treatment algorithm is provided.

26 Claims, 7 Drawing Sheets

Treatment Protocol for Management of the Hemodynamically Unstable Patient

ROC Curve for Predicting >15% Increase in Cardiac Output in Septic Shock Patients

USE OF AORTIC PULSE PRESSURE AND FLOW IN BEDSIDE HEMODYNAMIC MANAGEMENT

GOVERNMENT CONTRACT

This work was supported in part by a grant from the NIH (NRSA 4-T32 HL07820-01A5).

CROSS-REFERENCE TO RELATED APPLICATION

This Application is a continuation-in-part Ser. No. 10/086,343 of the Application entitled "Use of Aortic Pulse Pressure and Flow in Bedside Hemodynamic Management", filed Mar. 1, 2002.

FIELD OF THE INVENTION

This invention relates to a treatment algorithm for managing hemodynamically unstable patients. Specifically, measurements of arterial pressure and stroke volume can be used to calculate pulse pressure variation, stroke volume variation, mean arterial pressure, elastance and cardiac power, the values of which guide treatment decisions.

BACKGROUND INFORMATION

The goal of cardiovascular therapy is to ensure that blood flow and oxygen delivery to the tissues is adequate to meet the metabolic demands of the tissues without inducing cardiorespiratory complications. Cardiovascular insufficiency is often referred to a circulatory shock, and is the primary manifestation of critical illness. In most clinical conditions associated with circulatory shock, the primary concerns and therapeutic options relate to three functional questions: 1) Will blood flow to the body increase if the patient's intravascular volume is increased, and if so, by how much is the cardiovasculature pre-load responsive? 2) Is any decrease in arterial pressure due to loss of vascular tone or due to inadequate blood flow? and 3) Is the heart capable of maintaining an effective blood flow with an acceptable perfusion pressure without going into failure?

Thus, in the assessment and management of critically ill patients, the immediate questions asked by doctors are functional and physiological in their language but practical and concrete in their application. Previously, highly invasive hemodynamic monitoring was needed to define the specific hemodynamic profiles seen in circulatory shock. Application of arterial elastance analysis was limited due to the difficulty of measuring beat-to-beat stroke volume at the bedside. Prior to the advent of esophageal pulsed Doppler and robust arterial pulse contour techniques, measurement of stroke volume on a beat-to-beat basis was not possible, and clinicians did not use this analysis as part of their diagnostic algorithms. Current diagnostic and treatment protocols do not directly address the questions asked above, even though the treatment of hemodynamically unstable patients can be resolved by answering these three questions.

For example, U.S. Pat. No. 5,551,435 discloses a method of obtaining a pre-selected combination of mean arterial pressure (MAP), stroke index (SI) and cardiac index (CI) in a patient. After MAP and SI are determined, the patient's deviation from ideal calculated values of MAP and SI can be determined, and administration of drugs and/or volume expanders is carried out to permit the patient's MAP and SI values to reach the desired ideal combination.

U.S. Pat. No. 5,584,298 discloses a non-invasive method for calculating actual stroke volume and cardiac output using computerized algorithms. Input data includes heart rate, blood pressure, sex, age, weight and height of the patient. Based on the input data, using the algorithm, actual cardiac stroke volume of the subject is calculated and displayed as output.

U.S. Pat. No. 5,865,758 discloses an algorithm that calculates stroke volume and cardiac output using a blood pressure pulse wave obtained from the subject, measured by means of an optical sensor clipped to the ear lobe of the patient. This patent does not teach or suggest using calculated values for variables such as PPV, etc. to provide a treatment algorithm as in the present invention.

U.S. Pat. No. 6,280,390 discloses a non-invasive method for measuring blood pressure by measuring blood volume in a blood vessel with infrared detectors.

None of the above methods use pulse pressure variation and stroke volume variation to guide selection of the appropriate treatment for a hemodynamically unstable patient, in need of immediate therapy.

SUMMARY OF THE INVENTION

The present invention provides a means of optimizing treatment of hemodynamically unstable patients, based on measurements of arterial pressure and stroke volume in a patient. Stroke volume variation, pulse pressure variation, mean arterial pressure, elastance and cardiac power can be calculated based on these measurements, and used to determine the optimal treatment for patients meeting certain criteria and classified as hemodynamically unstable.

In a further embodiment, the algorithm is implemented on a computer system. Any combination of hardware and software can be used to implement the algorithm, so long as the system includes apparatus for collecting both kinds of measurements (arterial pressure and stroke volume), a microprocessor apparatus for storing measurements and the software program containing the algorithm, and for calculating stroke volume variation, pulse pressure variation, mean arterial pressure, elastance and cardiac power, and a display apparatus for viewing the results.

Based on the measurements and the calculated variables, various treatment directives are provided to the physician. Such treatment directives comprise administering an intravascular fluid infusion, an inotropic drug, or a vasoactive drug.

It is an object of the present invention, therefore, to provide a treatment algorithm for managing hemodynamic instability based on measurements of arterial pulse pressure and stroke volume.

It is a further object of the invention to provide a treatment algorithm in which calculated values for pulse pressure variation (PPV), stroke volume variation (SVV), mean arterial pressure, elastance and cardiac power are used to guide selection of a treatment for a hemodynamically unstable patient.

It is an additional object of the invention to provide a computer system to implement the treatment system and provide treatment directives to the clinician.

These and other objects will become more readily apparent from the following figures, detailed description, examples and appended claims.

BRIEF DESCRIPTION OF THE DRAWINGS

The invention is further illustrated by the following non-limited drawings in which.

DETAILED DESCRIPTION OF PREFERRED EMBODIMENTS

The present invention provides a method of determining a treatment regimen for a hemodynamically unstable patient comprising:

a) obtaining arterial pressure and stroke volume measurements in the patient;

b) calculating pulse pressure variation, stroke volume variation, mean arterial pressure, elastance and cardiac power from the arterial pressure and stroke volume measurements; and c) providing a treatment algorithm based on the calculated values for pulse pressure variation, stroke volume variation, mean arterial pressure, elastance and cardiac power.

Treatment is administered to the patient, based on the treatment algorithm. The treatment comprises administering a fluid infusion, a vasoactive drug or an inotropic drug.

In another embodiment, the invention provides a method of electronically determining a treatment regimen for a hemodynamically unstable patient using a computer system. Such a system comprises providing a computerized data collection and analysis apparatus including a first collection apparatus for obtaining arterial pressure measurements in the patient, a second collection apparatus for obtaining stroke volume measurements in the patient, and a microprocessor apparatus for storing the measured data and a software program or programs containing the treatment algorithm and for calculating values for stroke volume variation, pulse pressure variation, mean arterial pressure, cardiac power and elastance, based on the measured data. The data collection and analysis apparatus would also include apparatus for displaying information related to the measurements, the calculated values and the treatment directives.

Arterial pressure and stroke volume measurements are collected from the patient, using the first and second collection apparatus. Stroke volume, as used herein, denotes the amount of blood ejected from the left ventricle of the heart per beat, or proportional flow per beat in the descending aorta, depending on the method of measurement. Pulse pressure variation, stroke volume variation, mean arterial pressure, elastance and cardiac power values are then calculated from the measurements using the microprocessor apparatus, and a treatment is selected based on the values of pulse pressure variation, stroke volume variation, mean arterial pressure, cardiac power and elastance. Output is displayed on any suitable device such as computer screen, paper and the like, showing the selected treatment regimen. As will be apparent to one skilled in the art, the algorithm is independent of any particular hardware or software system, and any suitable combination of hardware and software can be used to implement the algorithm according to the methods of the present invention.

The treatment directives include administration of a fluid infusion, or administration of a vasoactive or inotropic drug. Measuring arterial pressure change or aortic flow variation during positive-pressure breathing allows one to accurately predict if the patient's cardiac output will increase in response to fluid loading or decrease in response to increasing artificial ventilation support, thus permitting accurate delivery of potentially dangerous therapies.

As used herein, the term "vasoactive drug" refers to compounds which are used to modify blood pressure. Suitable compounds include, but are not limited to, norepinephrine, dopamine and epinephrine, and other vasodilators or vasoconstrictors known in the art. Usually, a vasopressor (vasoconstrictor) will be indicated, but in some circumstances, known to those skilled in the art, a vasodilator will be required. Methods of administration and dosage amounts for these compounds are known and well within the ability of one skilled in the art to determine.

As used herein, the terms "inotropic drug" or "inotrope" are interchangeable and refer to compounds which are given to modify the heart's ability to contract. Suitable compounds include, but are not limited to, dobutamine, milrinone, amrinone, calcium sensitizing agents, and the like. Again, dosage and routes of administration are known in the art for these compounds.

As used herein, the terms "bolus fluid infusion" or "intravascular fluid infusion" are interchangeable and are understood to refer to administration of fluids to one in need of increased blood volume. Suitable fluids include, but are not limited to, saline solution, Ringer's lactate solution, colloids, blood and the like. Administration of such fluids is well known in the art.

Arterial pulse pressure is the difference between the maximal arterial pressure (systolic pressure), and the minimum arterial pressure (diastolic pressure). For example, if a patients blood pressure is 120/80 then his pulse pressure would be 120 minus 80, or 40 mm Hg (actual pulse pressure varies slightly during breathing). If the variation in pulse pressure over a normal breath (tidal volume between 5 and 12 ml/kg) exceeds 10–15% of the baseline pulse pressure, then cardiac output will increase in response to intravascular volume challenges.

Figure 1:
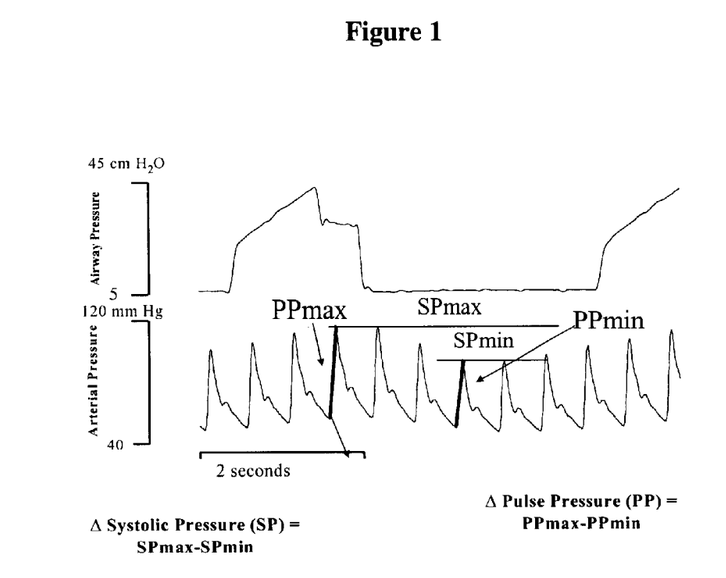
FIG. 1 is a strip chart recording of airway pressure and arterial pressure for a subject during positive pressure ventilation, illustrating the technique of calculating both systolic pressure variation (SPV) and pulse pressure variation (PPV).

Pulse pressure variation has been demonstrated to change inversely as cardiac output changes: it decreases as cardiac output increases with intravascular fluid loading, and increases as cardiac output decreases with increasing air pressure. Recent studies have demonstrated that aortic flow variation can also be used to determine preload-responsiveness and the subsequent change in cardiac output in response to a treatment. Thus, either arterial pulse pressure variation or aortic flow variation can be used to assess preload-responsiveness. An example of pulse pressure variation in a patient receiving artificial ventilation is shown in FIG. 1. Note that both systolic and diastolic arterial pressure vary with breathing. Measuring systolic pressure alone misrepresents this effect.

The pulse-pressure responsiveness index was validated under conditions in which the percent change in pulse pressure during ventilation was greater than about 10–15%. The size of the breath influences the magnitude of the change in venous return. Thus, if small breaths are given by artificial ventilation, then the maximum pulse pressure variation will also decrease, although the directional change in pulse pressure will still be accurate.

Figure 2:
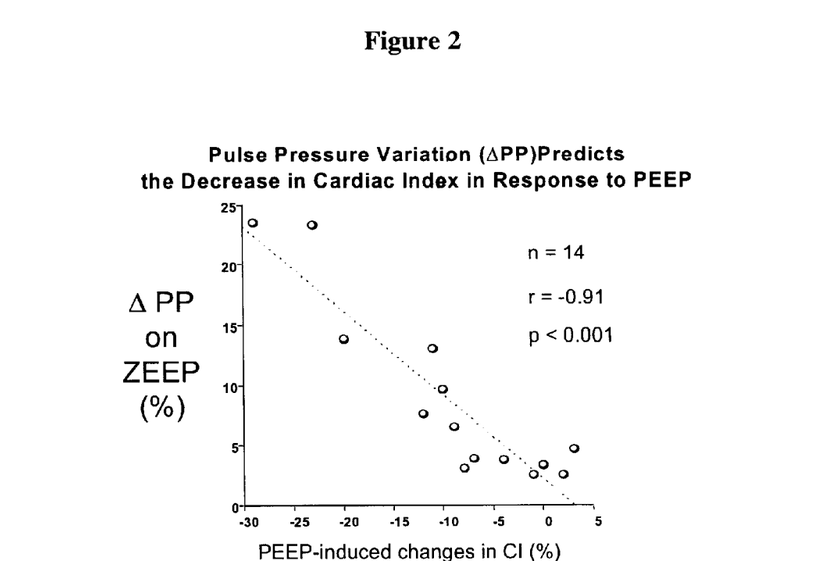
FIG. 2 is a prior art figure showing the relationship between 10 cm $H_2O$ PEEP-induced changes in cardiac index and initial PPV prior to the addition of PEEP.

Arterial pulse pressure variation also predicted the expected decrease in cardiac output in patients with acute lung injury who were given increasing amounts of positive airway pressure at end-expiration (PEEP). The relationship between pulse pressure variation and the change in cardiac output for these patients is shown in FIG. 2.

Figure 3:
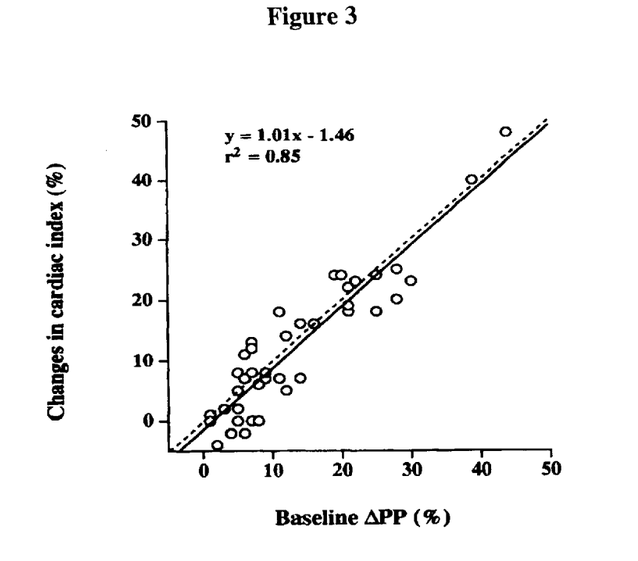
FIG. 3 is a prior art figure showing the relationship between change in cardiac index and initial PPV in septic patients given an intravenous bolus of 500 ml HES

In patients with severe septic shock, pulse pressure variation predicted the expected increase in cardiac output in response to intravascular fluid loading, as shown in FIG. 3: as pulse pressure variation decreased, cardiac output increased, so that changes in pulse pressure variation could be used to monitor the effect of intravascular volume loading on flow.

Figure 4:
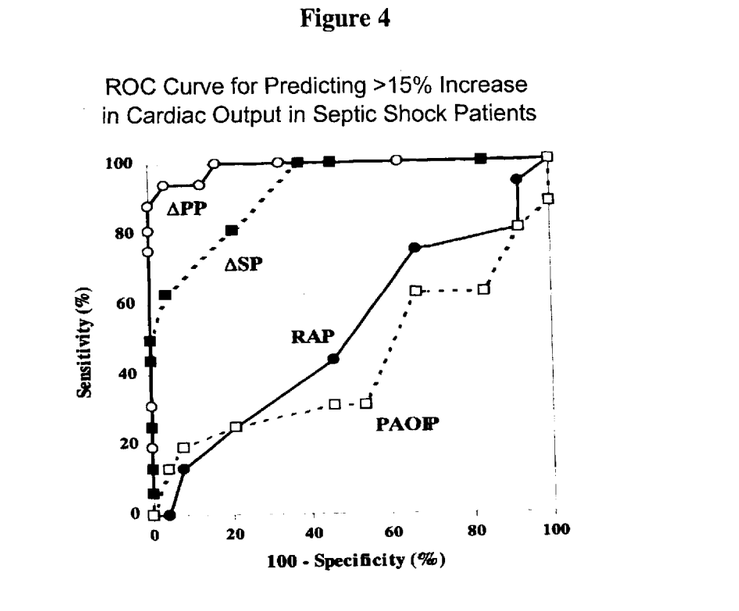
FIG. 4 is a prior art figure showing the receiver-operator characteristics of PPV, SPV, right atrial pressure (RAP) and pulmonary artery occlusion pressure (PAOP) to predict a greater than 15% increase in cardiac output in response to a 500 ml HES challenge.

The predictive ability of pulse pressure variation was compared to other methods of assessing hemodynamic status and pre-load responsiveness, such as 1) pulse pressure variation, 2) systolic pressure variation, 3) measures of absolute right atrial pressure, and 4) pulmonary artery occlusion pressure, using receiver-operator characteristic analysis. As can be seen from the ROC analysis (FIG. 4), the pulse pressure variation analysis was superior to all others with minimal false positive or false negative results.

Critically ill patients often have low blood pressure (hypotension), which can be a very serious condition because it causes an immediate decrease in blood flow to the heart and brain. If hypotension is profound and sustained for more than a few minutes, irreversible damage will occur to the brain and heart, making full recovery impossible.

Blood pressure is determined not only by cardiac output, but also by the tone of the arteries. Many diseases cause the arteries to loose their tone, referred to as vasodilation, which also creates a hypotensive state; thus hypotension can be caused by either low cardiac output or loss of vasomotor tone, or a combination of the two. However, treatment of hypotension depends upon the cause, and is made more difficult by the fact that the body alters vasomotor tone, if it can, to keep blood pressure as constant as possible. Measuring blood pressure alone does not indicate the cause of hypotension or how to treat it.

Even if cardiac output is above normal, systemic hypotension will impair blood flow regulation and pressure-dependent flow to all organs. Thus, knowledge of vasomotor tone and its change in response to vasoactive therapy is also relevant in deciding on the appropriate therapy.

It has been found that the same measures of arterial pulse pressure and aortic flow variation during a positive-pressure breath can be used to determine arterial tone, which can be characterized by the ratio of change in arterial pulse pressure to change in stroke volume. This value allows for the continual tracking of vascular tone as treatment or time evolve.

Figure 5:
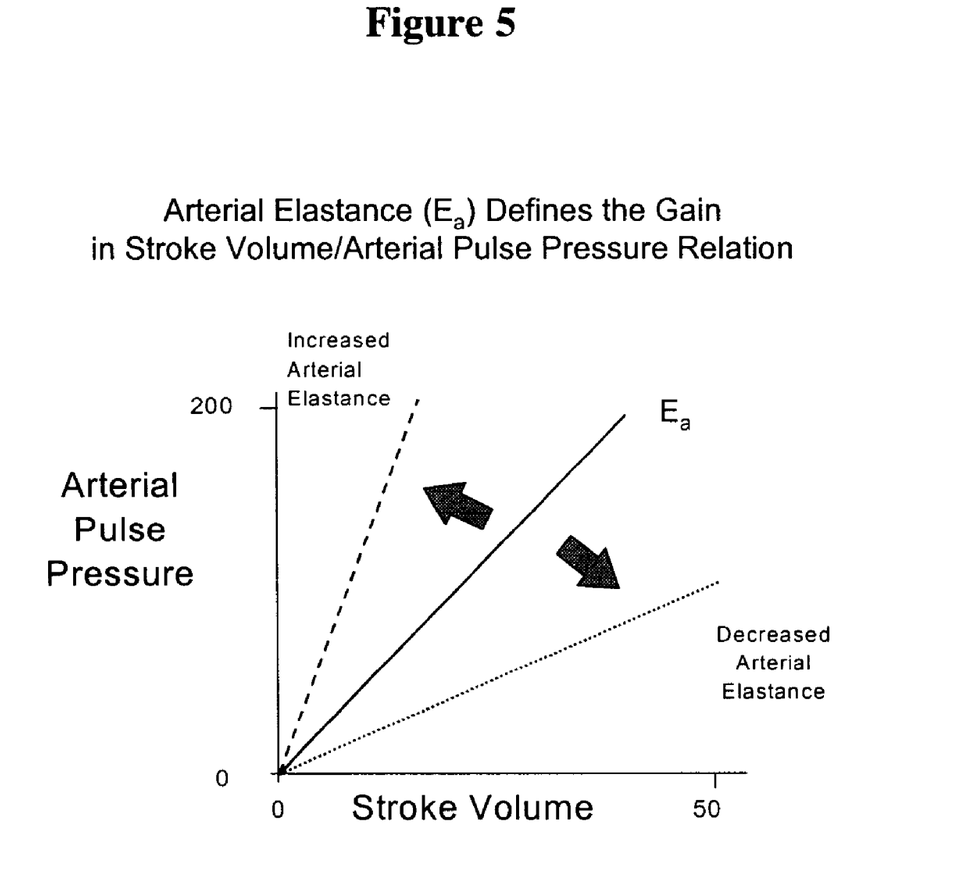
FIG. 5 shows the effect of changes in arterial vasomotor tone on the relationship between arterial pulse pressure and stroke volume.

For a given stroke volume, an increase in arterial tone causes a proportionate increase in arterial pulse pressure and in the ratio of pulse pressure to stroke volume. If stroke volume doubles, then pulse pressure will also double. As can be seen in FIG. 5, increasing tone increases the "slope" of the pressure to flow relationship. Thus, by measuring the ratio of arterial pulse pressure to aortic flow during breathing, one can easily derive an accurate measure of arterial tone. The term "elastance" is often used to describe a phasic flow system, and is used herein to denote the ratio of arterial pulse pressure to stroke volume.

In addition to cardiac output and blood pressure, information on cardiac pump performance is needed for management of critically ill patients. Knowledge of contractile reserve helps predict a patient's response to subsequent stress (such as weaning from mechanical ventilation or surgery), the ability of the patient to sustain adequate cardiac output if arterial pressure is increased, and in following the heart's response to treatments aimed at improving contractility (coronary vasodilation during ischemia, dobutamine infusion).

The best measures of contractility are those that are not affected by changes in either cardiac size just prior to contraction (end-diastole), or by pressure and muscle tension needed to develop the ejection pressure during contraction (afterload). Cardiac contractility measures include LV end-systolic elastance, preload-recruitable stroke work, and preload-adjusted maximal cardiac power. The use of these in the routine monitoring and management of critically ill patients is impractical because they require invasive cardiac catheterization or continuous imaging at bedside using highly trained personnel.

Alternatively, both the product of peak aortic flow-arterial pressure or stroke volume and arterial pressure are excellent measures of maximal cardiac power, and can be made from instantaneous stroke volume and arterial pressure data. If cardiac power is below a certain minimal level, and the patient is preload-responsive, then volume should be given. If the patient is not preload-responsive, then low cardiac power clearly identifies the heart as a primary cause of circulatory shock and critical illness. Diagnostic efforts and treatments must focus on improving cardiac performance. In such a situation, the treatment algorithm of the present invention directs the physician to start an inotropic agent and/or perform a more directed diagnostic study on the heart, such as insertion of a flow-directed pulmonary artery catheter or performing an echocardiographic study. One skilled in the art will be able to recognize when further diagnostic studies are needed; impaired myocardial contractility could be an indication for ischemia or infarction, hypoxemeia, hypoglycemia, hypothermia, or an electrolyte balance. Similarly, impaired myocardial pumping could be an indication for valvulopathy or arrythmias, and impaired left ventricle filling could be indicative of tamponade, tension pneumothorax, hyperinflation, diastolic dysfunction, cor pulmonale, or pulmonary embolism.

The relationship between simultaneously measured aortic stroke volume and pulse pressure and their changes during breathing provides accurate beat-to-beat assessment of preload-responsiveness, arterial tone and effective cardiac power that can be used to rapidly diagnose and treat most forms of cardiovascular insufficiency to a degree of accuracy and precision not previously available. Since over one-quarter of the entire health care budget is applied to patients who develop cardiovascular insufficiency, and effective prevention of sustained cardiovascular insufficiency has been shown to reduce mortality and expensive and debilitating complications, the implications of this simple approach are profound.

A component of the analysis is the measurement of arterial pulse pressure. Several devices can measure arterial pressure and its pulse pressure components. For example, pressure can be measured using an indwelling arterial catheter inserted into a femoral or radial artery. A pressure transducer is used to convert pressure to an electrical signal. Arterial pulse pressure can also be measured non-invasively using an optic distortion meter attached to the fingertips. A device known by the tradename Finepres is commercially available for this purpose. Arterial pulse pressure can also be measured by use of an arterial impedance blood pressure cuff. From these signals, diastolic, systolic and mean arterial pressure on a beat-to-beat basis can be calculated. As used herein, the term "first collection apparatus" refers to any method or device, including but not limited to those methods or devices described herein, which can be used to measure arterial pressure.

The other data input is stroke volume, either absolute or relative. Several systems are available to measure this variable. Descending aorta flow can be measured directly by transesophageal pulse Doppler. This instrument will provide flow data, and also calculate stroke volume (flow over time). Stroke volume can also be inferred from the arterial pressure profile by a technique referred to as pulse contour analysis; devices which provide this analysis are available from numerous manufacturers. Either of these techniques can be used to measure beat-to-beat changes in stroke volume. Although the aortic flow signal is not equal to the absolute stroke volume, its variation in flow from beat to beat closely approximates the variation in left ventricular output. From these signals, stroke volume can be calculated on a beat-to-beat basis and used in combination with the arterial pulse pressure data described above. As used herein, the term "second collection apparatus" refers to any method or device which can be used to measure stroke volume, directly or indirectly, including, but not limited to those methods or devices described herein.

Based on the input data, several variables can be calculated, including:

Arterial pulse pressure (PP)=pressure difference between systolic and diastolic pressure
$PP_{max}$=maximal PP during a ventilatory cycle
$PP_{min}$=minimum PP during a ventilatory cycle
Stroke volume (SV)=left ventricle (LV) stroke volume, descending aortic flow per beat, or pulse contour-derived stroke volume used to estimate instantaneous LV output
$SV_{max}$=maximal SV during a positive-pressure breath
$SV_{min}$=minimum SV during a positive-pressure breath
Stroke work=stroke volume×systolic arterial pressure=SV× SAP Additional calculated variables include:

Mean arterial pressure (MAP)=Diastolic arterial pressure+ PP/3
Mean PP=$(PP_{max}+PP_{min})/2$
Mean SV+$(SV_{max}+SV_{min})/2$ Both pressure and flow variation are measured as a percentage of the mean pressure or flow during the breath, respectively:

Arterial pulse pressure variation (PPV)=positive-pressure ventilation-induced changes in arterial pulse pressure
PPV=$(PP_{max}-PP_{min})/[(PP_{max}+PP_{min})/2]\times 100$
Stroke volume variation (SVV)=positive-pressure ventilation-induced changes in stroke volume
SVV=$(SV_{max}-SV_{min})/[SV_{max}+SV_{min})/2]\times 100$
Arterial Elastance (Ea)=PPV/SVV Cardiac Power=SAP×peak flow (by the pulsed Doppler method), or MAP×SV÷heart rate (by pulse contour method).

Usual criteria for the diagnosis of hemodynamic instability include: (a) mean arterial pressure less than about 60 mm Hg and/or a decrease in mean arterial pressure of greater than about 20 mm Hg in a previously hypertensive patient, and at least one of (b) or (c): (b) evidence of end-organ hypoperfusion, such as a decrease in urine output to less than 20 ml/hr, confusion, new onset tachycardia, lactic acidosis, and ileus; and (c) symptoms of increased sympathetic tone such as agitation, confusion and restlessness. As used herein, the term "hemodynamically unstable" will refer to a patient who has met the above-listed criteria and is in need of treatment, using the methods of the present invention. A "patient" is any member of the of the animal kingdom, including but not limited to humans, who is under the care of a physician or veterinarian and in need of medical treatment.

Measurements of arterial pressure and stroke volume are made during positive-pressure breathing, and cardiac power, PPV and SVV are calculated as the average of measurements taken over three breaths. The patient must be breathing at a normal rate (minimal ventilatory settings required include a ventilatory mode of A/C, IMV≧10/min, or PS≧15 cm $H_2O$, with a tidal volume of 10 ml/kg and a frequency between 10 and 20/min). These measures may also be made during spontaneous ventilation if respiratory rate and tidal volume are uniform over time.

Only if hemodynamic instability is present will the physician proceed with the treatment algorithm. The treatment algorithm provides the clinician with the ability to manage pre-load responsiveness, arterial tone and perfusion pressure, and cardiac power in a hemodynamically unstable patient, by providing treatment directives based on the calculated values of PPV, SVV, cardiac power, Ea and MAP.

Figure 6:
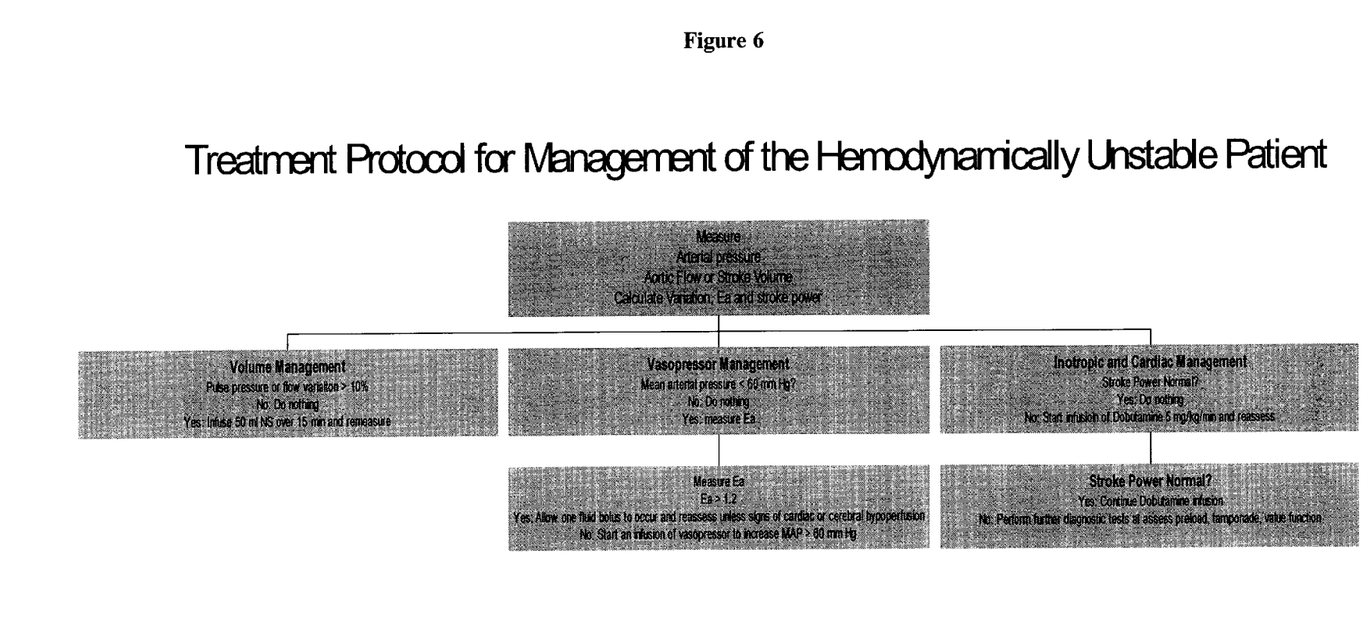
FIG. 6 is a flow diagram of the treatment algorithm.

The treatment algorithm is divided into two sequential treatment arms and one contingent treatment arm based on pulse pressure and flow variation during ventilation as well as the mean arterial pressure and flow. A flow diagram of the algorithm is shown in FIG. 6.

As used herein, the term "titration of drug therapy" means to increase or decrease (as in titrate upward or downward) the amount of drug administered over time. The amount of the increase will depend on the circumstances, taking into account the patient's age and overall condition. One skilled in the art will be able to determine the appropriate dosage and time intervals for administration of the vasoactive or inotropic drugs.

The steps are as follows:

Step 1. Measure arterial pressure and stroke volume during a positive pressure breath, over three breaths and average. Calculate values for pulse pressure variation, stroke volume variation, mean arterial pressure, cardiac power and elastance.

If either pulse pressure variation or stroke volume variation is greater than about 10%–15% then administer a bolus fluid infusion over the appropriate time interval and reassess pulse pressure or stroke volume variation. Repeat fluid infusions at appropriate intervals until pulse pressure variation becomes less than about 10%, at which time fluid is stopped. The appropriate interval will depend on a variety of factors such as age of the patient, prior condition, and the like; determination of the appropriate interval for administration of additional fluids is well within the ability of one skilled in the art to determine.

If mean arterial pressure remains less than about 55–65 mm Hg, more preferably about 60 mm Hg, or there is a decrease in mean arterial pressure of greater than about 15–25 mm Hg, more preferably about 20 mm Hg, in a previously hypertensive patient, after the initial fluid bolus then start the vasoactive (in this case vasopressor) protocol as described in step 3 below.

Step 2. Calculate the slope of the pulse pressure variation to stroke volume variation (elastance). If elastance is greater than about 1.2 then the patient has increased arterial tone, and fluid resuscitation alone should rapidly increase mean arterial pressure. Vasopressor should be withheld during the initial fluid bolus.

If elastance is less than about 0.8 then the patient should be simultaneously started on a vasopressor and titrated upward over appropriate time intervals to increase mean arterial pressure to greater than about 55–65 mm Hg.

If elastance is less than about 1.2 but greater than 0.8 initial vasopressor therapy may be given, at the discretion of the physician, to maintain mean arterial pressure greater than about 55–65 mm Hg.

When elastance becomes greater than about 2, further increases in the vasopressor infusion rate should be stopped until the next fluid bolus is given, assuming the pulse pressure variation remains greater than about 10–15%.

Step 3. Once pulse pressure variation or stroke volume variation becomes less than about 10–15%, if vasopressor therapy is still required (to keep mean arterial pressure greater than about 55–65 mm Hg) calculate cardiac power. If cardiac power is not within the normal range, then cardiac performance is impaired. Inotropic therapy should be started, with pulse pressure variation (or stroke volume variation) and elastance reassessed at appropriate intervals. If persistent depression of cardiac performance is present, titrate the inotrophic therapy upwards at appropriate intervals.

Step 4. Measure arterial pressure and stroke volume at additional time intervals to monitor the patient's condition over time. Disease progression or response to specific interventions can be monitored in a patient by assessing the changes in stroke volume and pulse pressure over time. For example, an increase in both pulse pressure and stroke volume indicates an increase in preload responsiveness, contractility, or both, while a decrease in PP and SV indicates a decrease in one or both of these measures. If pulse pressure increases with a corresponding decrease in stroke volume, there has been an increase in arterial tone; if PP decreases with a corresponding increase in SV, then there has been a decrease in arterial tone. One skilled in the art will be able to determine the appropriate time intervals for reevaluation of the condition of the patient. As used herein, the term "additional time intervals" will be used to denote monitoring the patient over additional time intervals, determined by one skilled in the art as necessary to assess changes in contractility, preload responsiveness and arterial tone.

Typical normal values for cardiac power are values over about 3000 mm Hg cm (using stroke distance as measured by esophogeal pulsed doppler) or 500 mg Hg ml (using the pulse contour measure of stroke volume).

If hemodynamic insufficiency persists, then assess cardiac function directly by use of a balloon floatation pulmonary artery catheter and/or echocardiographic study, and treat the patient based on the invasive monitoring findings. Using this approach, pulmonary artery catheters are not be inserted early during resuscitation but will be used when specific diagnostic information related to cardiac performance is needed.

As will be apparent to one skilled in the art, the values presented above as decision points for pulse pressure variation, elastance, cardiac power, and mean arterial pressure are not hard and fast values but rather are presented as guidelines for the treating physician. For example, a physician may decide to administer a fluid infusion when mean arterial pressure is slightly higher than 60 mm Hg, taking into account other factors of the patient's condition. Further, a hospital implementing the treatment algorithm as a therapy protocol may decide that the optimal decision points, based on its patient population, are slightly higher or slightly lower than those presented herein.

EXAMPLES

The following examples are intended to illustrate the invention and should not be construed as limiting the invention in any way.

Example 1 - Hemorrhagic Shock

A 56 year old Hispanic farmer with a history of adult onset diabetes, hypercholesterolemia and mild hypertension presents to the emergency room with a two day history of abdominal pain, nausea and over the past day and half black tarry stools. Since this morning, he has felt extremely lightheaded and nearly collapsed when trying to stand upon arising. On exam, he is distraught, BP is 100/30, mean 58 mm Hg, heart rate 110 with an increase in HR to 135 and decrease in BP mean to 45 mm Hg with sitting. While a diagnostic evaluation is proceeding to identify the cause of this problem, the measures of arterial pulse pressure by an indwelling arterial catheter and stroke volume by an esophageal pulsed Doppler monitor are instituted using the treatment algorithm. The initial measures are shown in the panel opposite and command the physician to give volume and reassess in 15 minutes.

Figure 7:
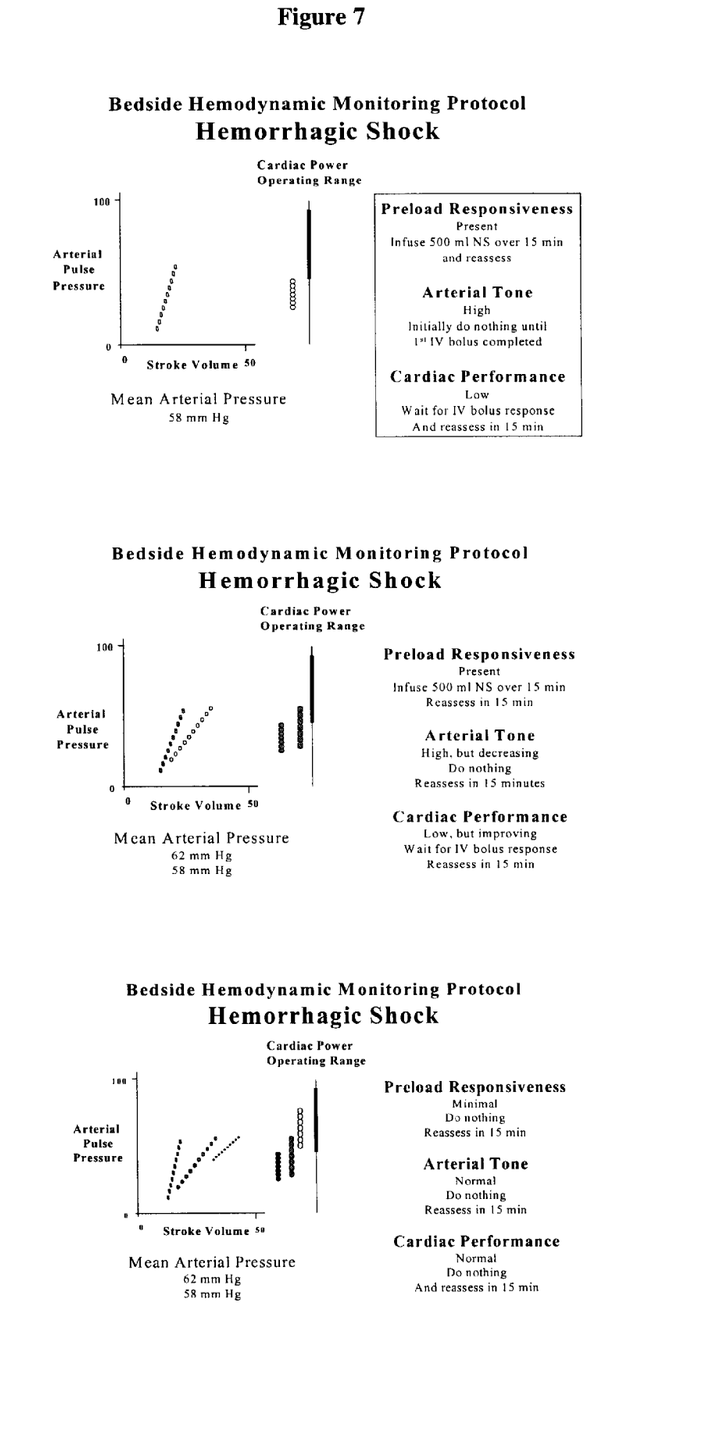
FIG. 7 shows use of the algorithm for a patient in hemorraghic shock.

The repeat measures at 15 minutes show that blood pressure is increasing and heart rate decreasing, but the patient is still tachycardic with postural signs so the treatment algorithm commands the patient received additional fluid therapy as described in FIG. 7. The PPV/SVV slope is decreasing, consistent with a decrease in heightened arterial tone, and low cardiac power is also improving as expected, assuming hypovolemia is being appropriately treated. Repeat measures are requested in 15 minutes.

The second set of repeat measures now show that mean arterial pressure is in an acceptable range, heart rate is now normal and both arterial tone and cardiac power are normal. The treatment algorithm commands the physician to do no resuscitation and reassess in another 15 minutes.

While this resuscitation is proceeding in an orderly manner, appropriate diagnostic procedures are proceeding in parallel. A nasogastric tube is inserted and reveals only minimal coffee ground material, which rapidly clears on saline lavage. An emergency endoscopy is performed, identifying and an actively bleeding ulcer 2×1.5 cm in size in the second stage of the duodenum and cauterized. Laboratory studies reveal a hemoglobin of 7 gm % and a hematocrit of 23%. The subject is transfused two units of packed red blood cells and sent to the ward for further observation. He was subsequently discharged home on anti-ulcer therapy the following day.

Example 2 - Cardiogenic Shock

A 64 year old retired secretary with a 25 pack-year smoking history, social alcohol intake and a positive family history for coronary artery disease was seen by her gynecologist for bloody spotting and by Pap smear and punch biopsy found to an a cervical carcinoma. Her other complaints were swelling of her ankles that had increased markedly over the past few months. She was admitted to the hospital and following a negative work up for metastasis successfully underwent a vaginal hysterectomy. She initially did well, until the second post-operative day when she complained of severe chest pain, profound shortness of breath and a near syncopal episode. On evaluation, she is grossly cyanotic in obvious respiratory distress with a heart rate of 105.

Figure 8:
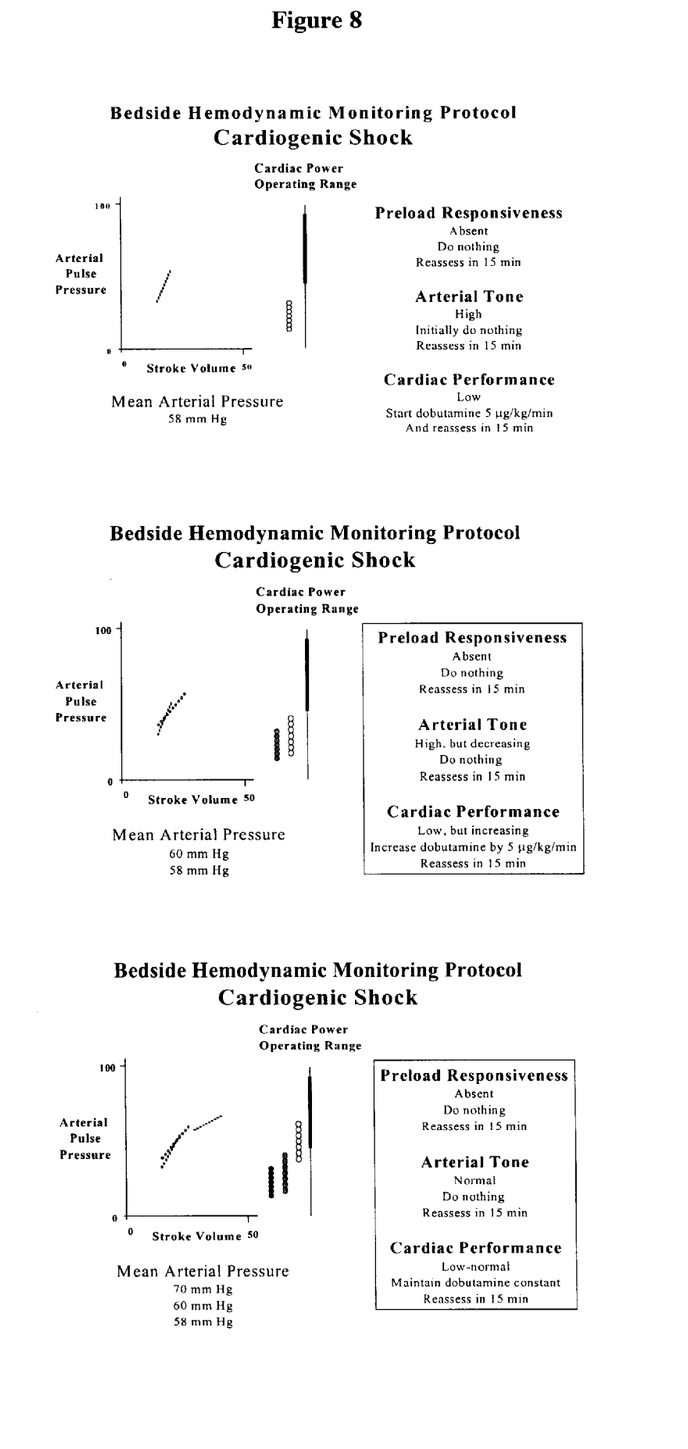
FIG. 8 shows use of the algorithm for a patient in cardiogenic shock.

The acute response team was called and intubated her tracheal and immediately transferred her to the surgical intensive care unit. Wherein she was found to be hypotensive, tachycardic but with $SpO_2>98\%$ on an $FiO_2$ of 0.5. She was placed on mechanical ventilatory support, had an arterial catheter inserted to monitor her pressure and an esophogeal pulsed Doppler inserted to assess her descending aortic flow. The initial data from those measures are displayed on the panel opposite. Note that although she has hypotension and an increased arterial tone, both her PPV and SVV are <10%, thus she is not preload-responsive. Based on the treatment algorithm, the physicians are commanded to start an inotrope (in this case dobutamine) and to reassess her in 15 minutes. This is shown in FIG. 8.

After 15 minutes, her blood pressure increased, her arterial tone decreased and her cardiac power increased. However, she was still not in the normal range, so the algorithm directed the physicians to increase dobutamine further and reassess once more in 15 minutes. This further increase in dobutamine resulted in a restoration of the patient's cardiovascular status, as demonstrated in the FIG. 8C.

While this stabilization algorithm was progressing, the patient was started on tissue plasminogen activator (tPA) that markedly reduced her pain and restored her ECG to normal. Because of lingering chest pain and ST segment depression, cardiac catheterization was performed and two stints were placed in the right coronary and left anterior descending arteries which displayed high-grade stenosis. By the second day post-catheterization, the patient was weaned off the dobutamine and returned to the floor. Cardiac enzymes documented a small myocardial infarction. The patient went on to have an uncomplicated recovery from both the surgery and cardiac stinting and was discharged home on the fifth hospital day.

Example 3 - Septic Shock

A twenty-two year old male brittle diabetic Caucasian college student presented to his PCP with a three-day history of fever, malaise and cough. The cough was initially non-productive but associated with pleuritic chest pain and diffuse myalgias. A chest radiograph revealed no infiltrates and a urine was positive for 2+ glucose and negative for ketones. He was treated with IV fluids, and a cepholosporin and sent home with instructions to return if his symptoms got worse. The following day his cough become productive of a yellow to brown blood tinged sputum and his fever remained. He delayed returning to his PCP, and that night he became more confused and agitated. His roommate brought him to the Emergency Department of the hospital where is was found to be in diabetic ketoacidosis as well as hypotensive, febrile (39.3° C.), tachypenic and hypotensive. His diabetes management consisted of starting an insulin infusion at 5 units/hr and fluid resuscitation. Because he became non-responsive his airway was electively intubated, he was placed on mechanical ventilation and transferred emergently to the medical intensive care unit. Besides being placed on broad-spectrum antibiotics following obtaining appropriate cultures of blood, urine and sputum an arterial catheter was inserted and a esophageal pulsed Doppler inserted to assess hemodynamic status.

Figure 9:
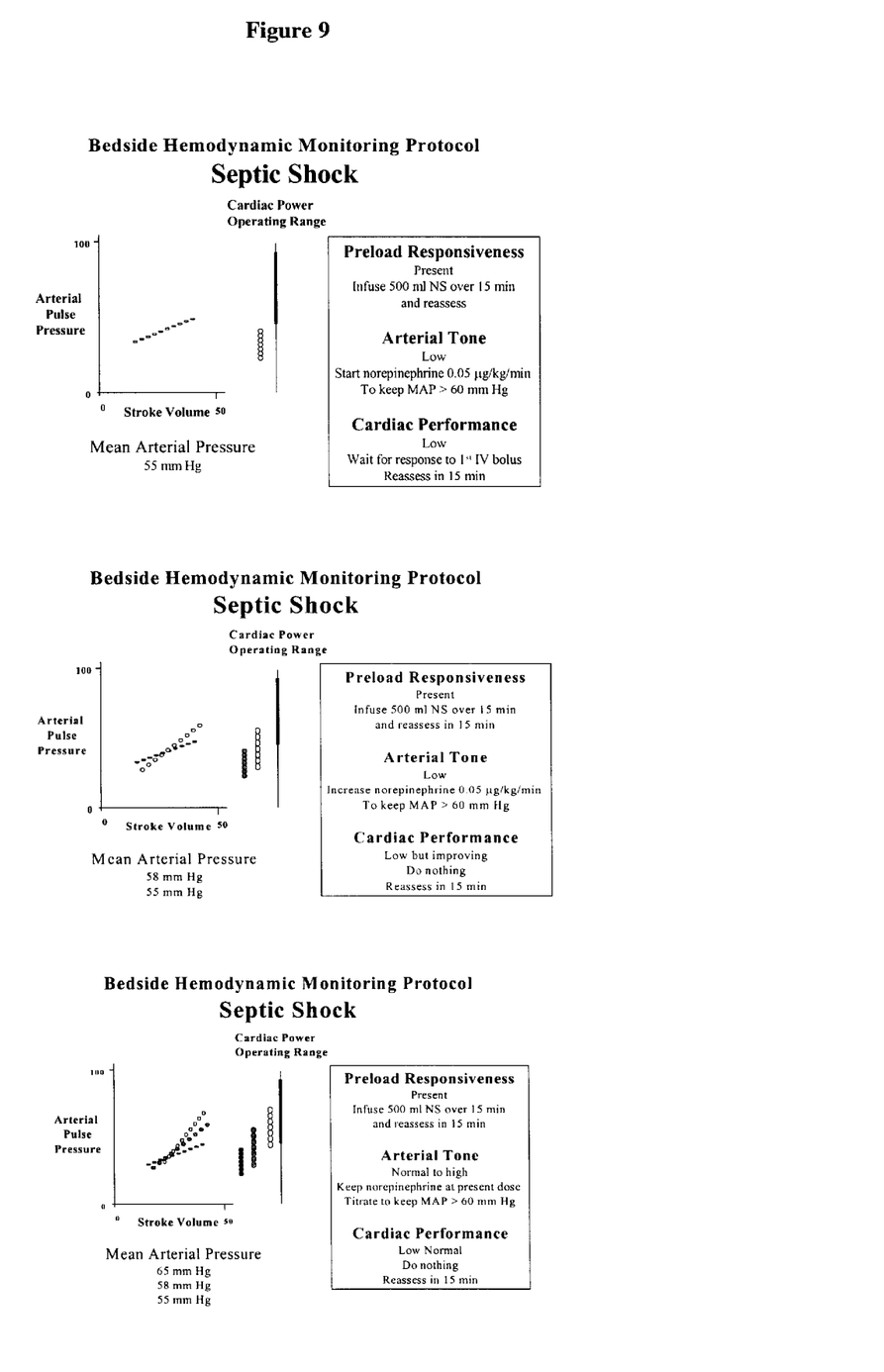
FIG. 9 shows use of the algorithm for a patient in septic shock.

The initial data was shown in FIG. 9A. He was hypotensive, tachycardic, with a wide SVV and minimal PVV consistent with a low arterial tone and preload-responsiveness. His cardiac power was also reduced. Because the arterial tone was reduced, vasopressor therapy was ordered by the protocol even though the patient was clearly preload-responsive. The logic of the algorithm being that even if the cardiac output were to increase with fluid resuscitation, arterial pressure would not increase as much, such that organ perfusion pressure would remain unacceptably low. Thus, both fluids and pressers were stared and the health care team instructed to re-evaluate in 15 minutes.

The subsequent hemodynamic data set, shown in the FIG. 9B, demonstrates that this initial therapy got things moving in the right direction, but did not achieve the end-goals of an adequate perfusion pressure. Specifically, arterial tone, mean arterial pressure and cardiac power all increased but remained below the normal values. Thus the protocol commanded the physicians to repeat the fluid bolus and also increase the vasopressor.

The final assessment after further increases in vasopressor and fluids demonstrated a persistent preload-responsiveness but now arterial tone, mean arterial pressure and cardiac power are normal. Thus, the algorithm commands the physicians to maintain vasopressor infusions as needed to keep mean arterial pressure at the present level while continuing to give further fluid boluses. This demonstrates the independence of fluid and vasopressor therapies.

The patient rapidly stabilized with resolution of the ketoacidosis and hemodynamic instability. The blood serology subsequently identified myoplasma pneunomae as the causative organism of the sepsis and the patient was discharged home.

The above examples demonstrate the robustness of the protocol's logic in managing complex hemodynamic processes simultaneously. Whereas particular embodiments of this invention have been described above for purposes of illustration, it will be evident to those skilled in the art that numerous variations of the details of the present invention may be made without departing from the invention as defined in the appending claims.

What is claimed is:

1. A method of determining a treatment regimen for a hemodynamically unstable patient comprising:

(a) obtaining arterial pressure and stroke volume measurements in said patient;

(b) calculating pulse pressure variation, stroke volume variation, mean arterial pressure, elastance and cardiac power from said measurements; and (c) providing a treatment algorithm based on said calculated values for pulse pressure variation, stroke volume variation, mean arterial pressure, elastance and cardiac power.

2. The method of claim 1, further comprising administering treatment to said patient, based on said treatment algorithm.

3. The method of claim 2, wherein said treatment comprises administering a fluid infusion to said patient.

4. The method of claim 2, wherein said treatment comprises administering a vasoactive drug to said patient.

5. The method of claim 2, wherein said treatment comprises administering an inotropic drug to said patient.

6. The method of claim 1, wherein said treatment algorithm comprises the following steps:
   (a) if either pulse pressure variation or stroke volume variation is greater than about 10%–15% then administering an initial fluid infusion and repeating fluid infusions until pulse pressure variation or stroke volume variation becomes less than about 10%; and
   (b) if mean arterial pressure remains less than about 55–65 mm Hg, or there is a decrease in mean arterial pressure of greater than about 15–25 mm Hg in a previously hypotensive patient, after said initial fluid infusion starting vasoactive therapy.

7. The method of claim 6, further comprising the following steps:
   (a) if elastance is greater than about 1.2 withholding vasoactive therapy during said initial fluid infusion;
   (b) if elastance is less than about 0.8 beginning vasoactive therapy at the same time as said initial fluid infusion and titrate vasoactive therapy upward until mean arterial pressure is greater than about 55–65 mm Hg; and
   (c) if elastance is less than about 1.2 but greater than about 0.8 giving initial vasopressor therapy, optionally, to maintain mean arterial pressure greater than about 55–65 mm Hg.

8. The method of claim 6, further comprising the following steps:
   (a) if pulse pressure variation or stroke volume variation become less than about 10–15% and vasoactive therapy is still needed to keep mean arterial pressure greater than about 55–65 mm Hg, if cardiac power is not within the normal range, beginning inotropic therapy; and
   (b) if cardiac power remains below normal, titrate titrating the inotrophic therapy upwards.

9. A method of electronically determining a treatment regimen for a hemodynamically unstable patient comprising:
   (a) providing a computerized data collection and analysis apparatus including a first collection apparatus for obtaining arterial pressure measurements in said patient,
      a second collection apparatus for obtaining stroke volume measurements in said patient,
      a microprocessor for storing said measurements and a software program containing said treatment regimen, and for calculating values for pulse pressure variation, stroke volume variation, mean arterial pressure, cardiac power and elastance, based on said measurements, and
      apparatus for displaying information related to at least one of said measurements, said calculated values and said treatment regimen;
   (b) using said first collection apparatus, collecting arterial pressure measurements from said patient;
   (c) using said second collection apparatus, collecting stroke volume measurements from said patient;
   (d) using said microprocessor apparatus, calculating pulse pressure variation, stroke volume variation, mean arterial pressure, elastance and cardiac power values from said measurements;
   (e) using said treatment regimen, selecting a treatment based on said measurements and said calculated values; and
   (f) providing output displaying said selected treatment regimen.

10. The method of claim 9, further comprising administering treatment to said patient, based on said selected treatment regimen.

11. The method of claim 10, wherein said treatment comprises administering a fluid infusion.

12. The method of claim 10, wherein said treatment comprises administering a vasoactive drug.

13. The method of claim 10, wherein said treatment comprises administering an inotropic drug.

14. The method of claim 9, wherein said treatment algorithm comprises the following steps:
   (a) if either pulse pressure variation or stroke volume variation is greater than about 10%–15% administering an initial fluid infusion and repeating fluid infusions until pulse pressure variation or stroke volume variation becomes less than about 10%; and
   (b) if mean arterial pressure remains less than about 55–65 mm Hg, or there is a decrease in mean arterial pressure of greater than about 15–25 mm Hg in a previously hypotensive patient, after said initial fluid infusion starting vasoactive therapy.

15. The method of claim 14, further comprising the following steps:
   (a) if elastance is greater than about 1.2 withholding vasoactive therapy during said initial fluid infusion;
   (b) if elastance is less than about 0.8 beginning vasoactive therapy at the same time as said initial fluid infusion and titrating vasoactive therapy upward until mean arterial pressure is greater than about 55–65 mm Hg; and
   (c) if elastance is less than about 1.2 but greater than about 0.8 giving initial vasopressor therapy, optionally, to maintain mean arterial pressure greater than about 55–65 mm Hg.

16. The method of claim 14, further comprising the following steps:
   (a) if pulse pressure variation or stroke volume variation become less than about 10–15% and vasoactive therapy is still needed to keep mean arterial pressure greater than about 55–65 mm Hg, if cardiac power is not within the normal range, beginning inotropic therapy; and
   (b) if cardiac power remains below normal, titrating the inotrophic therapy upwards.

17. A treatment algorithm for providing treatment of a hemodynamically unstable patient, said algorithm comprising the following steps:
   (a) obtaining arterial pressure and stroke volume measurements in said patient;
   (b) calculating pulse pressure variation, stroke volume variation, elastance and cardiac power from said measurements;
   (c) if either pulse pressure variation or stroke volume variation is greater than about 10%–15% administering an initial fluid infusion and repeating fluid infusions until pulse pressure variation or stroke volume variation becomes less than about 10%; and
   (d) if mean arterial pressure remains less than about 55–65 mm Hg, or there is a decrease in mean arterial pressure of greater than about 15–25 mm Hg in a previously hypotensive patient, after said initial fluid infusion starting vasoactive therapy.

18. The treatment algorithm of claim 17, further comprising the following steps:
   (a) if elastance is greater than about 1.2 withholding vasoactive therapy during said initial fluid infusion;

(b) if elastance is less than about 0.8 beginning vasoactive therapy at the same time as said fluid infusion and titrating vasoactive therapy upward until mean arterial pressure is greater than about 55–65 mm Hg; and (c) if elastance is less than about 1.2 but greater than about 0.8 giving initial vasopressor therapy, optionally, to maintain mean arterial pressure greater than about 55–65 mm Hg.

19. The treatment algorithm of claim 17, further comprising the following steps:

(a) if pulse pressure variation or stroke volume variation become less than about 10–15% and vasoactive therapy is still needed to keep mean arterial pressure greater than about 55–65 mm Hg, if cardiac power is not within the normal range, beginning inotropic therapy; and (b) if cardiac power remains below normal, titrating the inotrophic therapy upwards.

20. The treatment algorithm of claim 17, further comprising the following steps:

(a) obtaining arterial pressure and stroke volume measurements from said patient at additional time intervals; and (b) assessing contractility, arterial tone and preload responsiveness, based on said calculated values for pulse pressure variation, stroke volume variation, elastance and cardiac power.

21. A computer readable medium comprising computer readable program code including a treatment algorithm for treatment of a hemodynamically unstable patient, said treatment algorithm comprising the following steps:

(a) if either pulse pressure variation or stroke volume variation is greater than about 10%–15% administering an initial fluid infusion and repeating fluid infusions until pulse pressure variation or stroke volume variation becomes less than about 10%; and (b) if mean arterial pressure remains less than about 55–65 mm Hg, or there is a decrease in mean arterial pressure of greater than about 15–25 mm Hg in a previously hypotensive patient, after said initial fluid infusion starting vasoactive therapy.

22. The computer readable medium of claim 21 wherein said The treatment algorithm further comprises the following steps:

(a) if pulse pressure variation or stroke volume variation become less than about 10–15% and vasoactive therapy is still needed to keep mean arterial pressure greater than about 55–65 mm Hg, if cardiac power is not within the normal range, beginning inotropic therapy; and (b) if cardiac power remains below normal, titrating the inotrophic therapy upwards.

23. The computer readable medium claim 21 wherein said treatment algorithm further comprises the following steps:

(a) obtaining arterial pressure and stroke volume measurements from said patient at additional time intervals; and (b) assessing contractility, arterial tone and preload responsiveness, based on said calculated values for pulse pressure variation, stroke volume variation, elastance and cardiac power.

24. The computer readable medium of claim 21 wherein said treatment algorithm further comprises the following steps:

(a) if elastance is greater than about 1.2 withholding vasoactive therapy during said initial fluid infusion;

(b) if elastance is less than about 0.8 beginning vasoactive therapy at the same time as said initial fluid infusion and titrating vasoactive therapy upward until mean arterial pressure is greater than about 55–65 mm Hg; and (c) if elastance is less than about 1.2 but greater than about 0.8 giving initial vasopressor therapy, optionally, to maintain mean arterial pressure greater than about 55–65 mm Hg.

25. The microprocessor of claim 24 wherein said treatment algorithm further comprises the following steps:

(a) if pulse pressure variation or stroke volume variation become less than about 10–15% and vasoactive therapy is still needed to keep mean arterial pressure greater than about 55–65 mm Hg, if cardiac power is not within the normal range, beginning inotropic therapy; and (b) if cardiac power remains below normal, titrating the inotropic therapy upwards.

26. The microprocessor claim 24 wherein said treatment algorithm further comprises the following steps:

(a) obtaining arterial pressure and stroke volume measurements from said patient at additional time intervals; and (b) assessing contractility, arterial tone and preload responsiveness, based on said calculated values for pulse pressure variation, stroke volume variation, elastance and cardiac power.

* * * * *